US006466013B1

(12) United States Patent
Hawkes et al.

(10) Patent No.: US 6,466,013 B1
(45) Date of Patent: *Oct. 15, 2002

(54) NUCLEAR MAGNETIC RESONANCE MEASUREMENTS IN WELL LOGGING USING AN OPTIMIZED REPHASING PULSE SEQUENCE

(75) Inventors: Robert Hawkes, Cambridgeshire (GB); Robert Slade, Oxfordshire (GB); Alun Lucas, Cambridgeshire (GB)

(73) Assignee: Baker Hughes Incorporated, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 09/551,761

(22) Filed: Apr. 18, 2000

Related U.S. Application Data

(60) Provisional application No. 60/130,005, filed on Apr. 19, 1999.

(51) Int. Cl.[7] ............................................. G01V 3/00
(52) U.S. Cl. ........................................................ 324/303
(58) Field of Search .................................. 324/303, 307, 324/309

(56) References Cited

U.S. PATENT DOCUMENTS

| | | | |
|---|---|---|---|
| 5,023,551 A | 6/1991 | Kleinberg et al. | 324/303 |
| 5,248,942 A | 9/1993 | Ratzel et al. | 324/309 |
| 5,291,137 A * | 3/1994 | Freedman | 324/303 |
| 5,363,041 A | 11/1994 | Sezginer | 324/303 |
| 5,381,092 A * | 1/1995 | Freedman | 324/303 |
| 5,486,762 A * | 1/1996 | Freedman et al. | 324/303 |
| 5,680,043 A * | 10/1997 | Hurlimann et al. | 324/303 |
| 5,796,252 A * | 8/1998 | Kleinberg et al. | 324/303 |
| 6,121,774 A | 9/2000 | Sun et al. | 324/303 |
| 6,133,734 A * | 10/2000 | Mckeon | 324/303 |
| 6,163,153 A | 12/2000 | Reiderman et al. | 324/314 |
| 6,246,236 B1 * | 6/2001 | Poitzsch et al. | 324/303 |
| 6,331,775 B1 * | 12/2001 | Thern et al. | 324/303 |

FOREIGN PATENT DOCUMENTS

WO   WO 97/34167   9/1997

OTHER PUBLICATIONS

C. P. Slichter, *Principles of Magnetic Resonance*, Third Enlarged and Updated Edition, pp. 38–45.
Edwin D. Becker et al.; *Driven Equilibrium Fourier Transform Spectroscopy, A New Method for Nuclear Magnetic Resonance Signal Enhancement*, 5th Western Regional Meeting of the American Chemical Society, Anaheim, CA, Oct. 7, 1969.
R.R. Ernst; *Application of Fourier Transform Spectroscopy to Magnetic Resonance*, The Review of Scientific Instruments, pp. 93–102.

* cited by examiner

*Primary Examiner*—Edward Lefkowitz
*Assistant Examiner*—Dixomara Vargas
(74) *Attorney, Agent, or Firm*—Madan, Mossman & Sriram, P.C.

(57) ABSTRACT

A pulsed NMR tool has a magnet arrangement that is used to generate a static magnetic field having a substantially uniform field strength in a region of the formation surrounding the borehole. An RF coil is used to produce pulsed RF fields substantially orthogonal to the static field in the region of examination. The nuclear spins in the formation align themselves along the externally applied static magnetic field. A pulsed RF field is applied to tip the spins into the transverse plane, resulting in a precession of the spins. The tipping pulse is followed by a series of refocusing pulses and the resulting series of pulse echoes is detected. The timing and duration of RF pulses are altered from conventional CPMG to maximize signal and minimize RF power consumption. An additional forced recovery pulse at the end of an echo train may be used to speed up the acquisition and/or provide a signal for cancelling the ringing artefact.

37 Claims, 13 Drawing Sheets

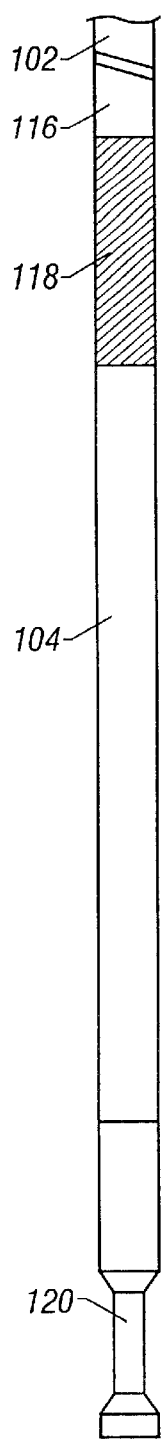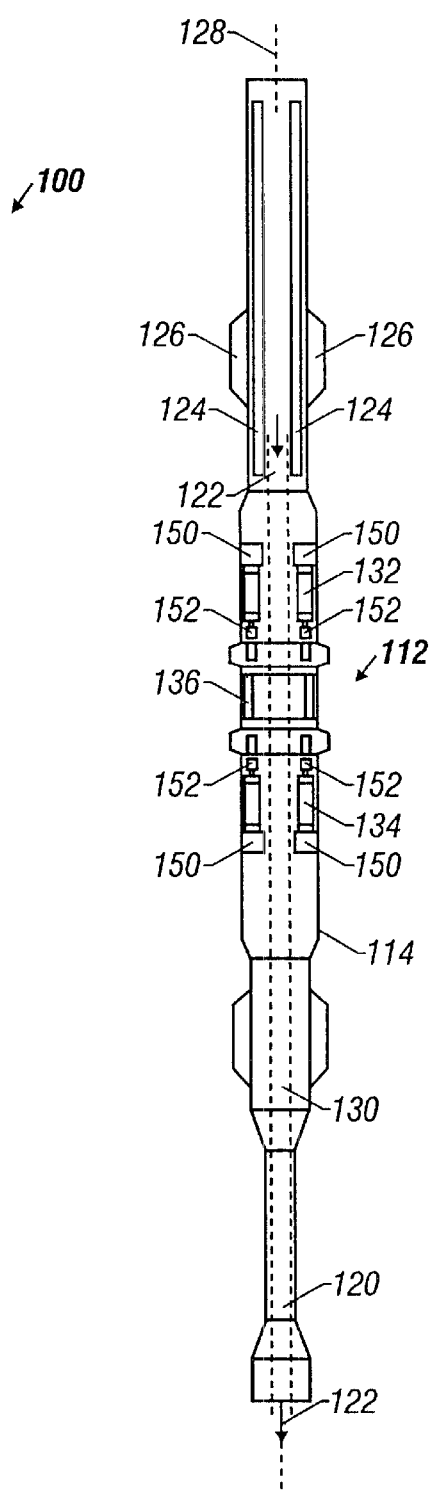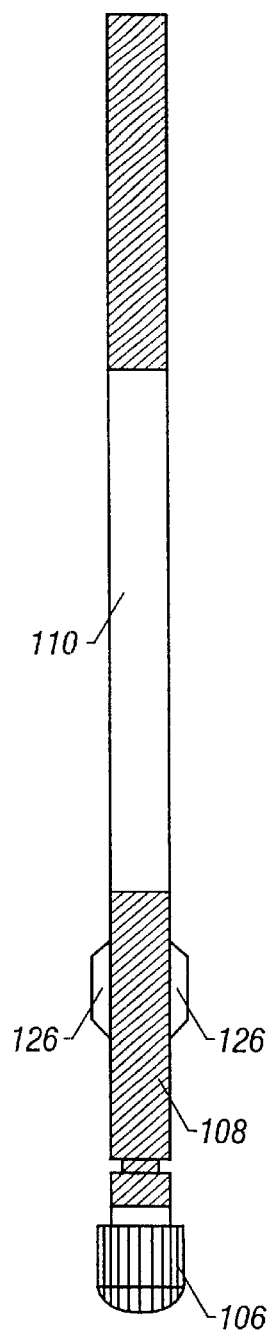
*FIG. 1A*  *FIG. 1B*  *FIG. 1C*

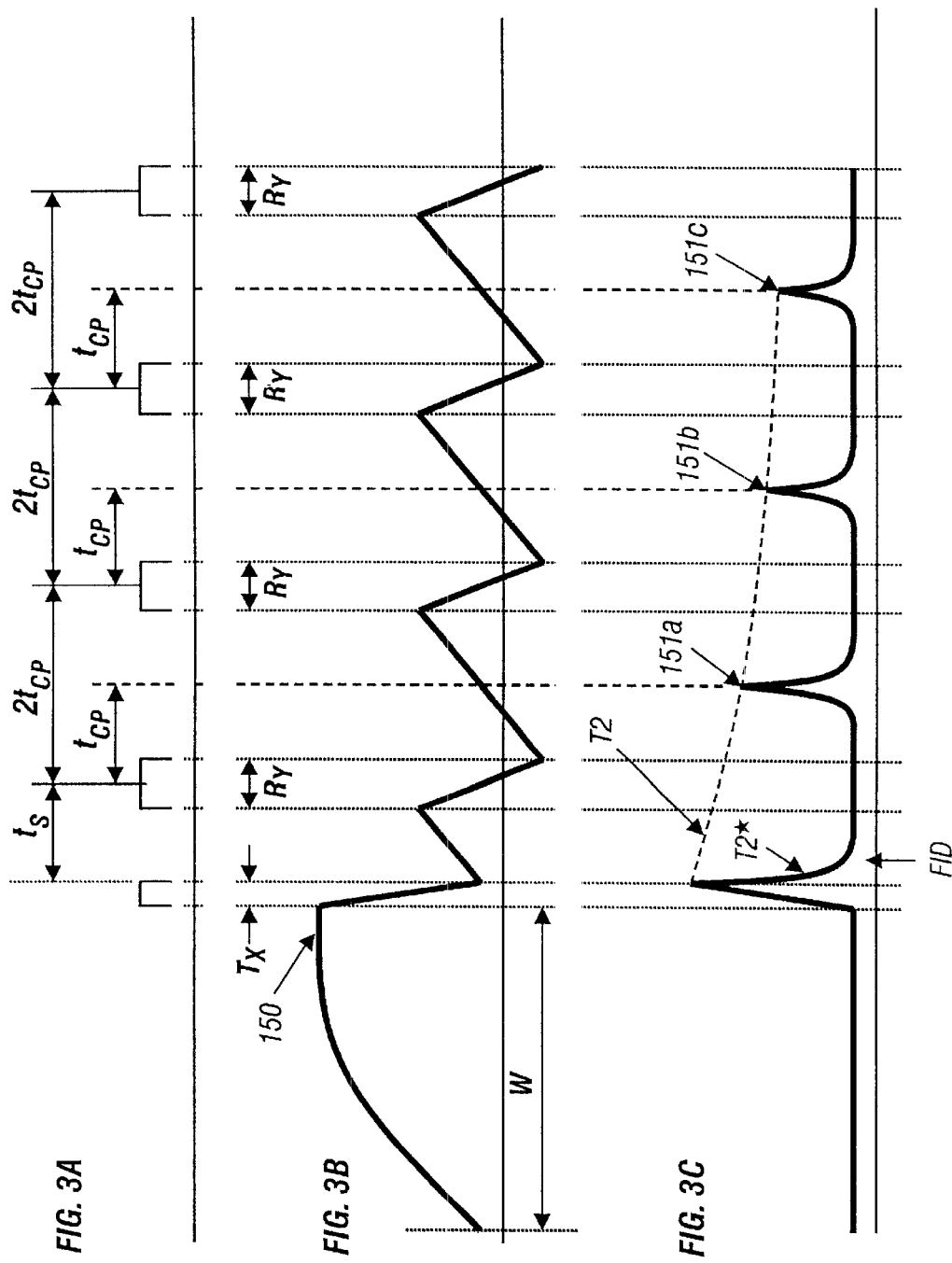

NUCLEAR MAGNETIC RESONANCE MEASUREMENTS IN WELL LOGGING USING AN OPTIMIZED REPHASING PULSE SEQUENCE

CROSS REFERENCES TO RELATED APPLICATIONS

This application claims priority from U.S. Provisional Patent Application Ser. No. 60/130,005 filed on Apr. 19, 1999.

BACKGROUND OF THE INVENTION

1. Field of the invention

This invention relates generally to determining geological properties of subsurface formations using Nuclear Magnetic Resonance (NMR) methods for logging wellbores, particularly for improving the signal level and reducing the power consumption by modifying the pulse sequence timing compared to prior art.

2. Background of the art

A variety of techniques are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One recently evolving technique involves utilizing Nuclear Magnetic Resonance (NMR) logging tools and methods for determining, among other things, porosity, hydrocarbon saturation and permeability of the rock formations. The NMR logging tools are utilized to excite the nuclei of the liquids in the geological formations surrounding the wellbore so that certain parameters such as spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR tools generate a uniform or near uniform static magnetic field in a region of interest surrounding the wellbore. NMR is based on the fact that the nuclei of many elements have angular momentum (spin) and a magnetic moment. The nuclei have a characteristic Larmor resonant frequency related to the magnitude of the magnetic field in their locality. Over time the nuclear spins align themselves along an externally applied magnetic field. This equilibrium situation can be disturbed by a pulse of an oscillating magnetic field, which tips the spins with resonant frequency within the bandwidth of the oscillating magnetic field away from the static field direction. The angle θ through which the spins exactly on resonance are tipped is given by the equation:

$$\theta = \gamma B_1 t_p \quad (1)$$

where γ is the gyromagnetic ratio, $B_1$ is the effective field strength of the oscillating field and $t_p$ is the duration of the RF pulse.

After tipping, the spins precess around the static field at a particular frequency known as the Larmor frequency $\omega_0$, given by $$\omega = \gamma B_0 \quad (2)$$

where $B_0$ is the static field intensity. At the same time, the spins return to the equilibrium direction (i.e., aligned with the static field) according to an exponential decay time known as the spin-lattice relaxation time or $T_1$. For hydrogen nuclei, $\gamma/2\pi = 4258$ Hz/Gauss, so that a static field of 235 Gauss would produce a precession frequency of 1 MHz. $T_1$ of fluid in pores is controlled totally by the molecular environment and is typically ten to one thousand milliseconds in rocks.

At the end of a θ=90° tipping pulse, spins on resonance are pointed in a common direction perpendicular to the static field, and they precess at the Larmor frequency. However, because of inhomogeneity in the static field due to the constraints on tool shape, imperfect instrumentation, or microscopic material heterogeneities, each nuclear spin precesses at a slightly different rate. Hence, after a time long compared to the precession period, but shorter than $T_1$, the spins will no longer be precessing in phase. This de-phasing occurs with a time constant that is commonly referred to as $T_2^*$ if it is predominantly due to the static field inhomogeneity of the apparatus, and as $T_2$ if it is due to properties of the material.

The receiving coil is designed so that a voltage is induced by the precessing spins. Only that component of the nuclear magnetization that is precessing in the plane perpendicular to the static field is sensed by the coil. After a 180° tipping pulse (or an "inversion pulse"), the spins on resonance are aligned opposite to the static field and the "precession" consists of a slow return along the static field axis to the equilibrium direction. Hence, a signal will be generated after a 90° tipping pulse, but not after a 180° tipping pulse in a generally uniform magnetic field.

While many different methods for measuring $T_1$ have been developed, a single standard known as the CPMG sequence (Carr-Purcell-Meiboom-Gill) for measuring $T_2$ has evolved. In contrast to laboratory NMR magnets, well logging tools have inhomogeneous magnetic fields due to the constraints on placing the magnets within a tubular tool and the inherent "inside-out" geometry. Maxwell's divergence theorem dictates that there cannot be a region of high homogeneity outside the tool. Therefore in typical well bores, $T_2^* \ll T_2$, and the free induction decay becomes a measurement of the apparatus-induced inhomogeneities. To measure the true $T_2$ in such situations, it is necessary to cancel the effect of the apparatus-induced inhomogeneities. To accomplish the same, a series of pulses is applied to repeatedly refocus the spin system, cancelling the T2* effects and forming a series of spin echoes. The decay of echo amplitude is a true measure of the decay due to material properties. Furthermore it can be shown that the decay is in fact composed of a number of different decay components forming a T2 spectrum. The echo decay data can be processed to reveal this spectrum which is related to rock pore size distribution and other parameters of interest to the well log analyst.

One method to create a series of spin echoes is due to Carr and Purcell. The pulse sequence starts with a delay of several T1 to allow spins to align themselves along the static magnetic field axis. Then a 90° tipping pulse is applied to rotate the spins into the transverse plane where they precess with angular frequency determined by local magnetic field strength. The spin system loses coherence with time constant, T2*. After a short time $t_{CP}$ a 180° tipping pulse is applied which continues to rotate the spins, inverting their position in the transverse plane. They continue to precess, but now their phases converge until they momentarily align a further time $t_{CP}$ after the 180° pulse. The 180° pulse is re-applied after a further time $t_{CP}$ and the process repeated many times forming a series of spin echoes with spacing 2 $t_{CP}$.

While the Carr-Purcell sequence would appear to provide a solution to eliminating apparatus induced inhomogeneities, it was found by Meiboom and Gill that if the duration of the 180° pulses in the Carr-Purcell sequence were even slightly erroneous so that focusing is incomplete, the transverse magnetization would steadily be rotated out of the transverse plane. As a result, substantial errors would enter the T2 determination. Thus, Meiboom and Gill devised a modification to the Carr-Purcell pulse sequence such that after the spins are tipped by 90° and start to de-phase, the carrier of the 180° pulses is phase shifted by $\pi/2$ radians relative to the carrier of the 90° pulse. This phase change causes the spins to rotate about an axis perpendicular to both the static magnetic field axis and the axis of the tipping pulse. If the phase shift between tipping and refocusing pulses deviates slightly from $\pi/2$ then the rotation axis will not be perfectly orthogonal to the static and RF fields, but this has negligible effect. For an explanation, the reader is referred to a detailed account of spin-echo NMR techniques, such as "NMR: a nuts and bolts approach", Fukushima and Roeder. As a result any error that occurs during an even numbered pulse of the CPMG sequence is cancelled out by an opposing error in the odd numbered pulse. The CPMG sequence is therefore tolerant of imperfect spin tip angles. This is especially useful in a well logging tool which has inhomogeneous and imperfectly orthogonal static and pulse-oscillating (RF) magnetic fields, U.S. Pat. No. 5,023,551 issued to Kleinberg discloses an NMR pulse sequence for use in the borehole environment which combines a modified fast inversion recovery (FIR) pulse sequence with a series of more than ten, and typically hundreds, of CPMG pulses according to $$[W_i-180_x-t_i-90_x-(t_{cp}-180_y-t_{cp}-\text{echo})_j]_i \qquad (3)$$

where j=1,2, . . . ,J, and J is the number of echoes collected in a single CPMG sequence, where i=1,2, . . . ,I and I is the number of waiting times used in the pulse sequence, where $W_i$ are the recovery times before the inversion pulse, and where $t_i$ are the recovery times before a CPMG sequence, and where $t_{CP}$ is the Carr-Purcell spacing. The phase of the RF pulses 90 and 180 is denoted by the subscripts X and Y, Y being phase shifted by $\pi/2$ radians with respect to X. The subscripts also conventionally relate to the axis about which rotation of the magnetization occurs during the RF pulse in a local Cartesian co-ordinate system centered on the nucleus in which the static magnetic field is aligned in the Z direction and the RF field in the X direction. This sequence can be used to measure both T1 and T2, but is very time consuming, limiting logging speed. If $t_{CP}$ is set to zero and the inverting pulse is omitted then the sequence defaults to standard CPMG for measuring T2 only.

A number of other prior art inventions, such as those disclosed in U.S. Pat. No. 5,363,041 issued to Sezginer, U.S. Pat. No. 5,381,092 issued to Freedman, and International Application WO 97/34167 of Prammer use variations of the CPMG pulse sequence. Fundamental to all of these inventions is the use of a 180° refocusing pulse.

The CPMG pulse sequence was developed for use in laboratory and medical settings where the magnets are outside the region of examination and it is relatively easy to maintain a uniform magnetic field strength over the region of examination. In a downhole NMR system, the magnetic field inevitably has a substantial magnetic field gradient compared to a laboratory magnet. This is a direct and unavoidable result of its "inside-out" nature: the region of examination is on the outside of the magnets. In order to maximize the NMR signal from such a system, it is necessary to gather the signal from a region as large as possible. To do this, the magnetic field gradients are minimized over a volume of space remote from the tool. However, the remaining magnetic field inhomogeneity is still hundreds to thousands of times larger than in a laboratory magnet. Therefore, the RF pulse bandwidth must be as large as possible to tip nuclei with resonance conditions as far as possible from the resonant frequency, thereby expanding the volume boundaries to the maximum possible.

To achieve a wide bandwidth, the RF pulses must be as short as possible, consistent with the available RF peak power, typically a few kilowatts, which leads to the condition that the 90° pulse is shorter than the 180° refocusing pulse, and is typically half the duration if the pulses have an approximately square shaped envelope. Consequently, the 90° pulse has twice the bandwidth of the 180° pulse. As a result of this only about half the nuclei which are tipped by the 90° pulses are subsequently refocused by the 180° pulse.

The above discussion is an over-simplification because of the substantial inhomogeneity and non-orthogonality of the real static and RF fields, but it captures the essence of the problem of using a CPMG sequence in an inhomogeneous field system.

SUMMARY OF THE INVENTION

The present invention is a method of improving the NMR signals received from a formation surrounding a borehole. Any pulsed NMR tool in which a magnet arrangement is used to generate a static magnetic field having a substantially uniform field strength in a region of the formation surrounding the borehole, and in which an RF antenna is used to produce pulsed RF fields substantially orthogonal to the static field in the region of examination may be used. The nuclear spins in the formation align themselves along the externally applied static magnetic field. A pulsed RF field is applied which tips the spins on resonance by the desired tip angle for maximum signal, typically 90°. A refocusing pulse having a spin tip angle substantially less than 180° is applied with carrier phase shifted by typically $\pi/2$ radians with respect to the 90° tipping pulse. Although the refocusing pulses result in spin tip angles less than 180° throughout the sensitive volume, their RF bandwidth is closer to that of the original 90° pulse. Hence more of the nuclei originally tipped by 90° are refocused, resulting in larger echoes than would be obtained with a conventional 90° refocusing pulse. The reduced duration of the refocusing pulses also reduce the power consumption of the tool.

One embodiment of the invention uses a 90° pulse of inverted phase at the end of the sequence to speed up recovery of the longitudinal magnetization by forcing the realignment of the spin system with the static field, and to allow cancellation of the tipping pulse "ringing" artefact. The NMR echoes are analyzed in a conventional manner to give the NMR parameters of the formation.

BRIEF DESCRIPTION OF THE DRAWINGS

For a detailed understanding of the present invention, references should be made to the following detailed description of the preferred embodiment, taken in conjunction with the accompanying drawings, in which like elements have been given like numerals, wherein:

FIGS. 1A–1C are side elevation views partially in section, an exemplary drilling assembly including an NMR tool;

FIGS. 3A–3C are graphs of the optimized pulse sequence of the invention, and the resulting plots over time of the longitudinal magnetization ($M_z$, FIG. 3B) and one component of transverse magnetization ($M_x$, FIG. 3C) and the measurable signal (FIG. 3C);

DETAILED DESCRIPTION OF PREFERRED EMBODIMENTS

Figure 2:
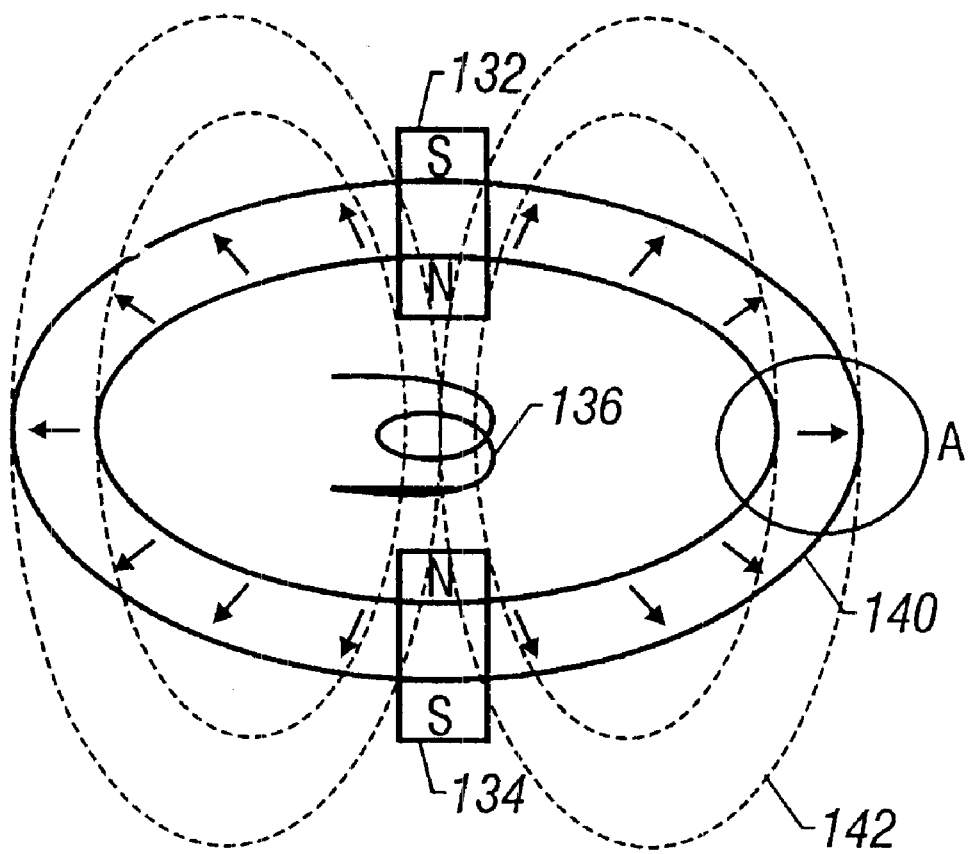
FIG. 2 (PRIOR ART) illustrates the production of a toroidal region of homogeneous radial magnetic field perpendicular to a pair of axially aligned magnets having like adjacent poles and the application of a pulsed RF field to the magnetization.

Referring to FIGS. 1A–1C, an exemplary drilling assembly 100 at the end of a drillstring 102 or coiled tubing is illustrated. A measurement-while-drilling (MWD) tool 104, an associated pulsed nuclear magnetic resonance (NMR) tool 112 (contained within a housing 114) and electronic circuitry 124, and a pulsed power unit 118 are connected in tandem in the drilling assembly 100. Flex subs 120 are used for example in connecting the MWD tool 104 and the NMR tool 112 in the drilling assembly 100. The MWD tool 104 may also include a sonic sensor, a density measurement tool, and a porosity measurement tool. A communication sub 116 using, for example, two-way telemetry, is also provided as illustrated in the drilling assembly 100.

The drilling assembly 100 includes a drill bit 106, bearing assembly 108, and downhole mud motor 110. The drillstring 102 includes, for example, sections of drill pipe connected end-to-end or a generally continuous coil. The borehole typically contains a drilling fluid 122 or "mud" which is forced through the drill string 102 and the bottom hole drilling assembly 100 through the drill bit 106. A channel 130 within the drill string 102 and drilling assembly 100 allows the drilling fluid 122 through the drill string 102 and drilling assembly 100. The drilling fluid acts to lubricate the drill bit 106 and to carry borehole cutting or chips away from the drill bit 106.

The communication sub 116, power unit 118, MWD tool 104, and NMR tool 112 are all connected in tandem with the drillstring 102. Such subs and tools form a bottom hole drilling assembly 100 between the drillstring 102 and the drill bit 106. Stabilizers 126 are used to stabilize and center the drilling assembly and tools within the borehole. The housing 114, for example, a drilling collar, is made of a non-magnetic alloy. The drilling assembly 100 makes various measurements including pulsed nuclear magnetic resonance while the borehole is being drilled. As seen in FIG. 1B, the NMR tool is rotationally symmetric about a longitudinal axis 128 of the drilling assembly 100. This is not to be construed as a limitation and the method of the present invention may be used with any prior art device used for obtaining NMR measurements in the subsurface of the earth. Furthermore, while an MWD embodiment of the present invention has been shown, the method of the present invention may also be used in wireline logging, logging while drilling and in logging while tripping, as these terms are understood by those versed in the art.

The pulsed NMR tool 112 includes at least two spaced-apart magnets 132 and 134 housed in the drilling assembly 100 and within the NMR tool 112 for producing a static magnetic field having a region of substantially uniform magnetic intensity in the vicinity of the borehole. The at least two spaced-apart magnets 132 and 134 illustrated in FIG. 2 are tubular in shape and arranged co-axially within the NMR tool 112 and to surround the channel 130. A radio frequency (RF) transmitting antenna or coil 136 also surrounds the channel 130, and is located, for example, between the two spaced-apart magnets 132 and 134. The RF coil 136 is connected to a suitable RF pulse transmitter for providing power at selected frequencies and a processor 124 which determines the pulse sequence timing. The RF coil 136 is pulsed and creates a high frequency RF field orthogonal to the static magnetic field.

The at least two magnets 132 and 134 are permanently magnetized, for example, in the axial direction and, in one embodiment, are positioned in opposing directions, as shown in FIG. 2. As shown in FIG. 2, like magnetic poles, for example, the north magnetic poles of the two magnets 132 and 134 face one another for producing a toroidal region of homogeneous radial magnetic field 140 perpendicular to the pair of axially aligned magnets 132 and 134. The pulsed RF coil 136 creates the pulsed RF field 142 illustrated by dashed lines. The distance of the toroidal region 140 of homogeneous radial magnetic field from the axis of the magnets 132 and 134 is dependent upon the strength of the magnets 132 and 134, and the distance between like poles of the magnets 132 and 134. Rock pores (not shown) in the earth formations are filled with fluid, typically water or hydrocarbon. The hydrogen nuclei in the fluid are aligned in the region of homogeneous magnetic field 140, generated by the magnets 132 and 134. The hydrogen nuclei are then "flipped" away from the homogeneous magnetic field 140 by the pulsed RF field 142 produced by RF coil 136. At the termination of the pulsed RF field from coil 136, the hydrogen nuclei revolve or precess at high frequency around the homogeneous magnetic field 140 inducing an NMR signal in the RF coil 136 until the hydrogen nuclei relax to the original direction along the homogeneous magnetic field 140. The induced NMR signals are sent to the surface for processing or can be processed by a downhole processor (not shown).

Other configurations of magnets could also be used. For example, U.S. Pat. No. 4,710,713 issued to Shtriknan discloses a magnet arrangement in which the static field is produced by cylindrical magnets that have the north and south poles on the curved faces of the magnets, resulting in a static field of approximately dipole shape. The Shtrikman patent uses a rectangular loop antenna to produce a radio frequency field of similar dipole shape, but rotated by 90° with respect to the static field, thus maintaining the orthogonality between the static field and the RF field. Other variations would be known to those versed in the art, and any of these could be used in the present invention.

Turning to FIG. 3A the optimized pulse sequence of one embodiment of the present invention:

$$W-T_x-t_s-R_y-(t_{cp}-\text{echo}-t_{cp}-R_y)_j \quad (4)$$

is shown in graphical form. The subscripts X and Y denote the RF pulse phases and effective rotation axis in a local co-ordinate system centered on the nucleus with the static magnetic field oriented along the Z axis and RF magnetic field oriented approximately along the X axis, where phase Y is shifted by typically $\pi/2$ radians with respect to X. The subscript j denotes the index of the echo and refocusing pulse in the sequence. At the start of any sequence, after waiting for a period W, the spin system is at substantially zero transverse magnetization and a positive longitudinal magnetization ($M_Z$) which is equal to or less than the full equilibrium magnetization, as shown by the value 150 in FIG. 3B. The rate at which a nuclear spins align along the local static field axis (Z) during W is governed by the spin lattice relaxation time (T1). By adjusting the wait period W information relating to T1 can be obtained, as explained by Kleinberg and others.

Referring to FIGS. 3A–3C, at the end of period W a tipping pulse of duration T and phase X is applied to the formation, causing the spins at and near resonance condition to tip into the transverse (XY) measurement plane where they generate a free induction decay (FID) signal in the measurement coil of the borehole tool. The signal induced in the receiver coil by the $M_x$ component of transverse magnetization is shown in FIG. 3C. Because the dead-time of the borehole tool is on the order of fifty microseconds which is longer than the free induction decay time, the FID cannot generally be observed. If the wait time W is several times longer than the longest T1 of the formation fluids then the optimum tipping pulse is a pulse which results in a spin tip angle of 90° for spins on resonance. If W is shorter, such that full relaxation to equilibrium has not occurred, then the optimum spin tip angle is less than 90°, requiring a shorter pulse. This is the well known Ernst effect (Ernst R. R., Anderson W. A. Rev. Sci. Instrum. 37(1) 93 1966).

At a time $t_S$ after the T pulse, a refocusing pulse R is applied with phase Y (carrier phase shifted by typically $\pi/2$ with respect to X) and as seen in FIG. 3A, further refocusing pulses are applied every 2 $t_{CP}$ in accord with the sequence of eq. (4). The duration of R is such that the spin tip angle of all nuclei with resonance value within the bandwidth of the refocusing pulse is substantially less than 180°. This is in contrast to prior art methods wherein the duration of R is such that the spin tip angle associated with the refocusing pulse is 180°. These refocusing pulses act to reverse the de-phasing of the spin system in the transverse plane and thereby generate measurable echoes, indexed by j, at $2t_{CP}$ intervals after each refocusing pulse, as indicated in FIG. 3C. The magnitude of the echoes decays over a period of time. The rate of decay is dictated by the spin-spin or T2 relaxation parameter. The parameter T2 is of great interest to the log analyst as it contains information related to pore size distribution and other parameters of interest. By applying many refocusing pulses, numerous echo peak data points 151a, 151b, . . . are available for providing a decay curve indicative of T2.

In order to maximize the signal from the tipped nuclei, the RF pulses are always transmitted at maximum power, typically a few kilowatts, which in a downhole NMR tool leads to the condition that the 90° tipping pulse is typically half the duration of the 180° refocusing pulse used in CPMG (assuming that the pulses have a substantially square shaped envelope). Consequently, the 90° pulse has twice the bandwidth of the 180° pulse, and as a result, only about half the nuclei which are tipped by the 90° pulse are subsequently refocused by a 180° pulse. This reduction in the number of nuclei that are refocused is something not considered in prior art. This effect only occurs when gradients are present in the magnetic field, as is the case for all downhole NMR tools. All the prior art of record is aimed to making variations of the basic CPMG sequence with the purpose of reducing errors while keeping the refocusing pulse at 180°.

Figure 4A:
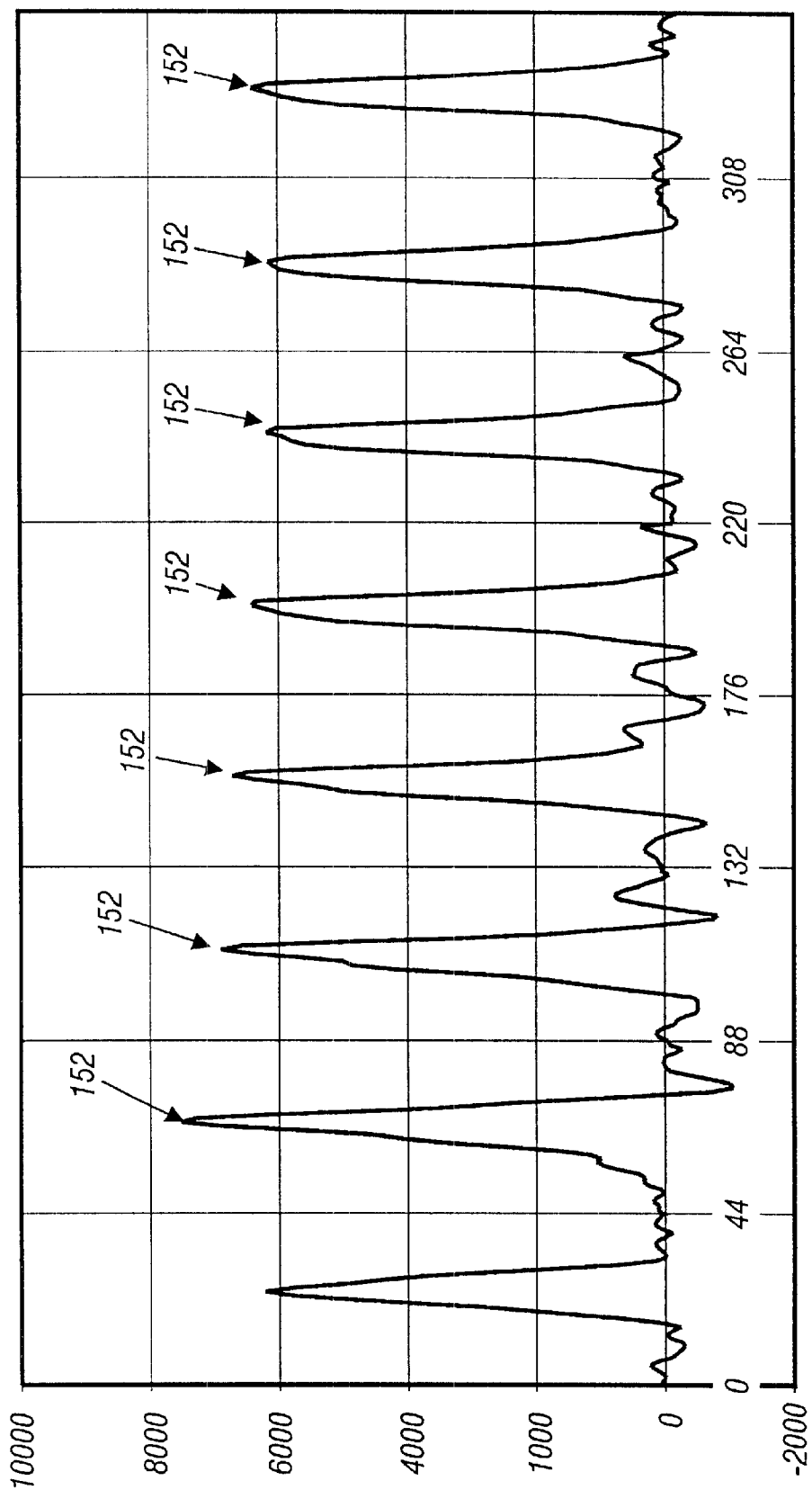
FIGS. 4A (PRIOR ART) to 4D are data plots showing a comparison of NMR echo signals using different duration refocusing pulses relative to the 90° tipping pulse, for experimental and simulated data.
Figure 4B:
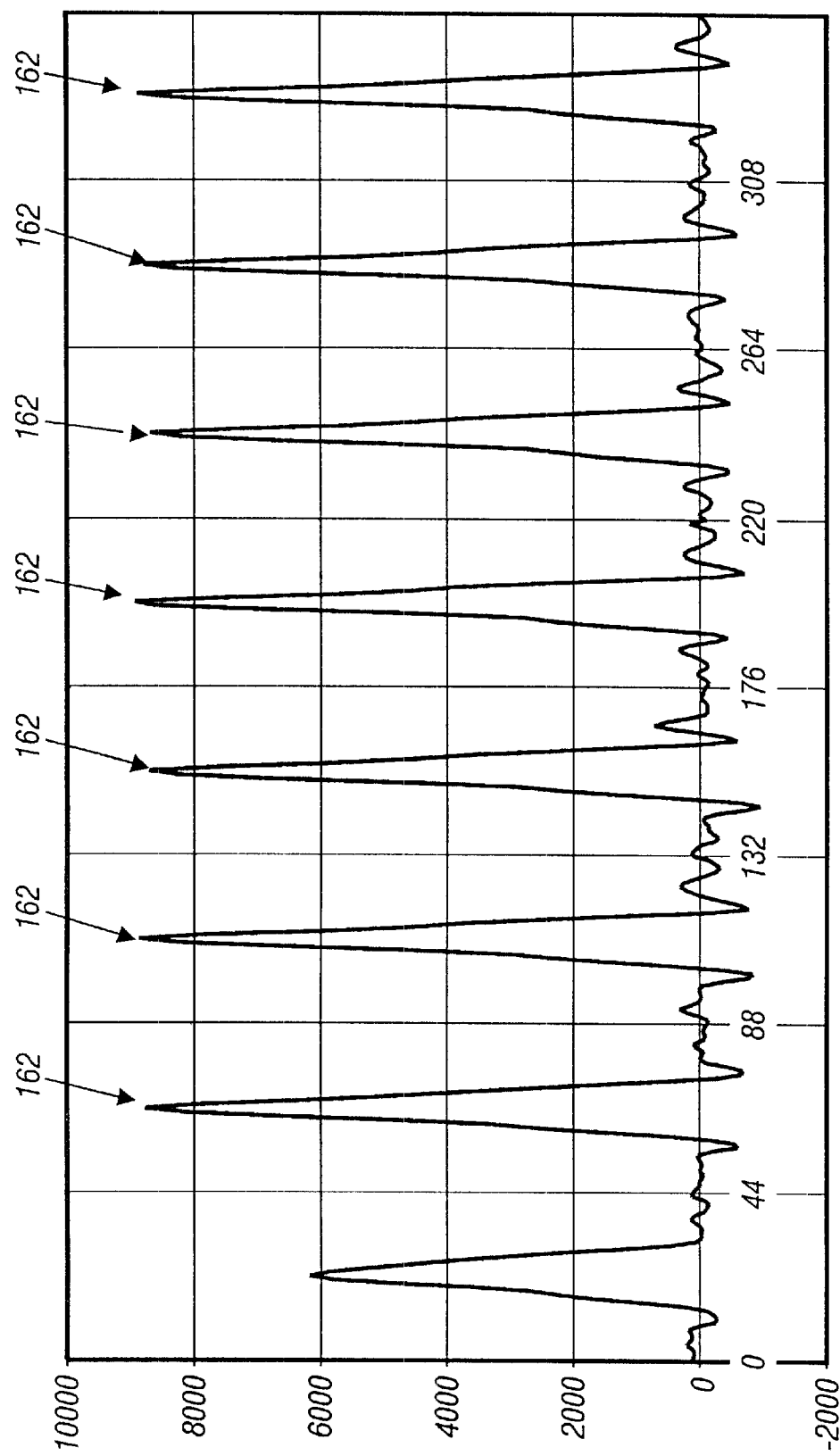

Turning now to FIGS. 4A and 4B, in which the ordinate for the display is the amplitude of the echo while the abscissa is time. Data in FIG. 4A was obtained using the CPMG sequence (prior art) with the tool immersed in a tank of water, simulating a borehole with 100% porosity. Data in FIG. 4B was obtained using the pulse sequence set out in eq. (4) with a refocusing pulse R of less than 180°. To obtain this data a NMR spectrometer system was used to demodulate the received signal in phase quadrature (real and imaginary components) using a continuous wave carrier reference signal equal to the Larmor frequency of the nuclei at the center of the sensitive volume; such a system is in common use and will be familiar to those skilled in the art. Using the spectrometer, data was acquired in time windows of 0.5 ms bracketing the echo, and the demodulated signal was digitized and recorded at 12 $\mu$s intervals. The data was then phase corrected according to traditional methods so that all echo information was in the real channel. FIGS. 4A and 4B show the concatenation of the real channel data from the first 8 windows recorded by this method, clearly displaying the echoes. The numbers along the abscissa are data point indices.

Before collecting the data, the T pulse was set accurately to 90° by varying the pulse length, using a refocusing pulse of approximately 90° and a CPMG sequence, with wait time W of 10 seconds, greater than five times the T1 of the measurement sample (tap water, T1~2s, T2~1s) to ensure complete relaxation, then seeking the maximum echo amplitude. Having set the T pulse, the refocusing pulse length R was varied and the echo trains acquired in phase alternated pairs (discussed below with reference to Table 1) and averaged over several measurements to improve the signal to noise ratio. The echo signal amplitude as shown in FIG. 4B corresponds to the maximum obtained when the R pulse length was equivalent to approximately 126° rotation. The peak amplitudes 162 in FIG. 4B are typically 25–30% greater than the peak amplitudes 152 for the CPMG sequence in FIG. 4A.; (FIGS. 4A and 4B have the same ordinate scale).

Figure 4C:
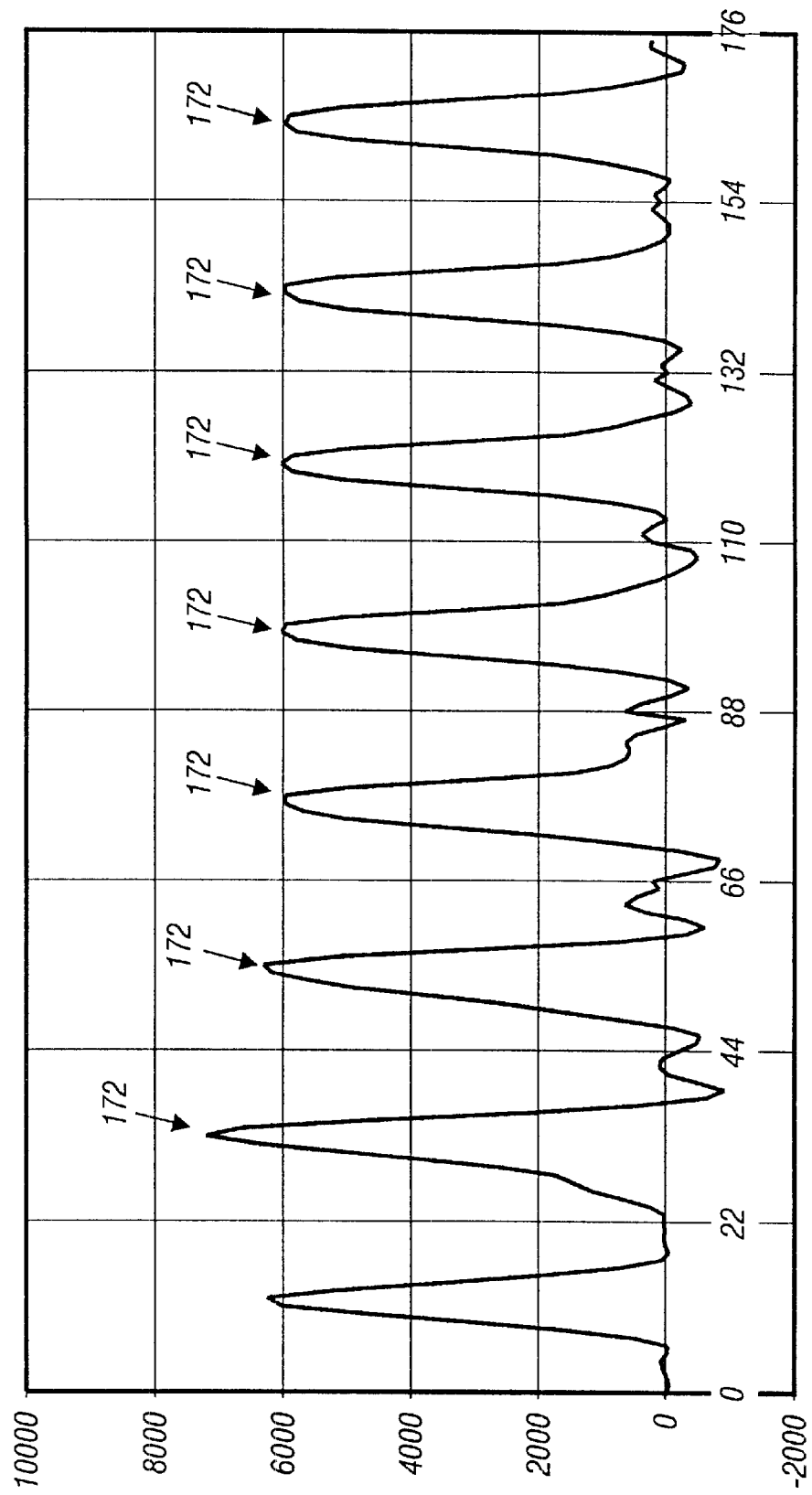
Figure 4D:
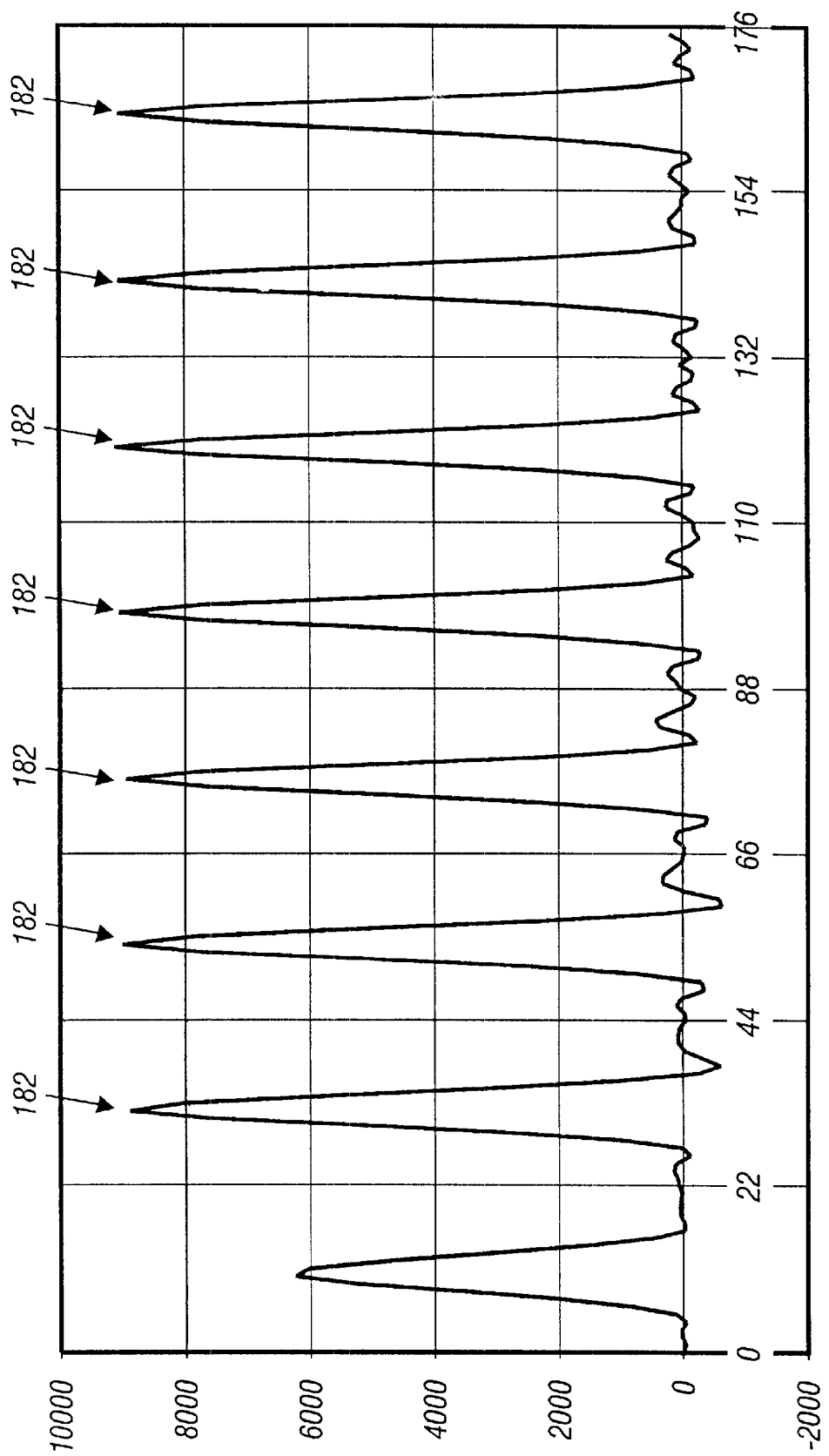

FIGS. 4C and 4D show simulation data for the same tool design obtained from a three dimensional spin dynamics numerical model of the sensor, on the same ordinate scale as FIGS. 4A and 4B. As in FIGS. 4A and 4B, the abscissa is time and the ordinate is the amplitude of the signal. The peak amplitudes 182 for the optimized pulse sequence are typically 25–30% greater than the peak amplitudes 172 for the simulated CPMG sequence. The spin dynamics model is described in Hancorn.

The optimum ratio between the durations of the refocusing and tipping pulses is hereby denoted by $\lambda$. In CPMG λ=2, but in the present invention λ<2. The optimum λ depends on the magnetic and RF field shapes, but is equal to 1.4 for the sensor design used for these tests.

The first echo of all the sequences shown in FIGS. 4A–4C is attenuated due to the well known "stimulated echo effect". This occurs in any pulsed NMR experiment conducted in an inhomogeneous magnetic field and the first echo should be ignored.

Figure 5A:
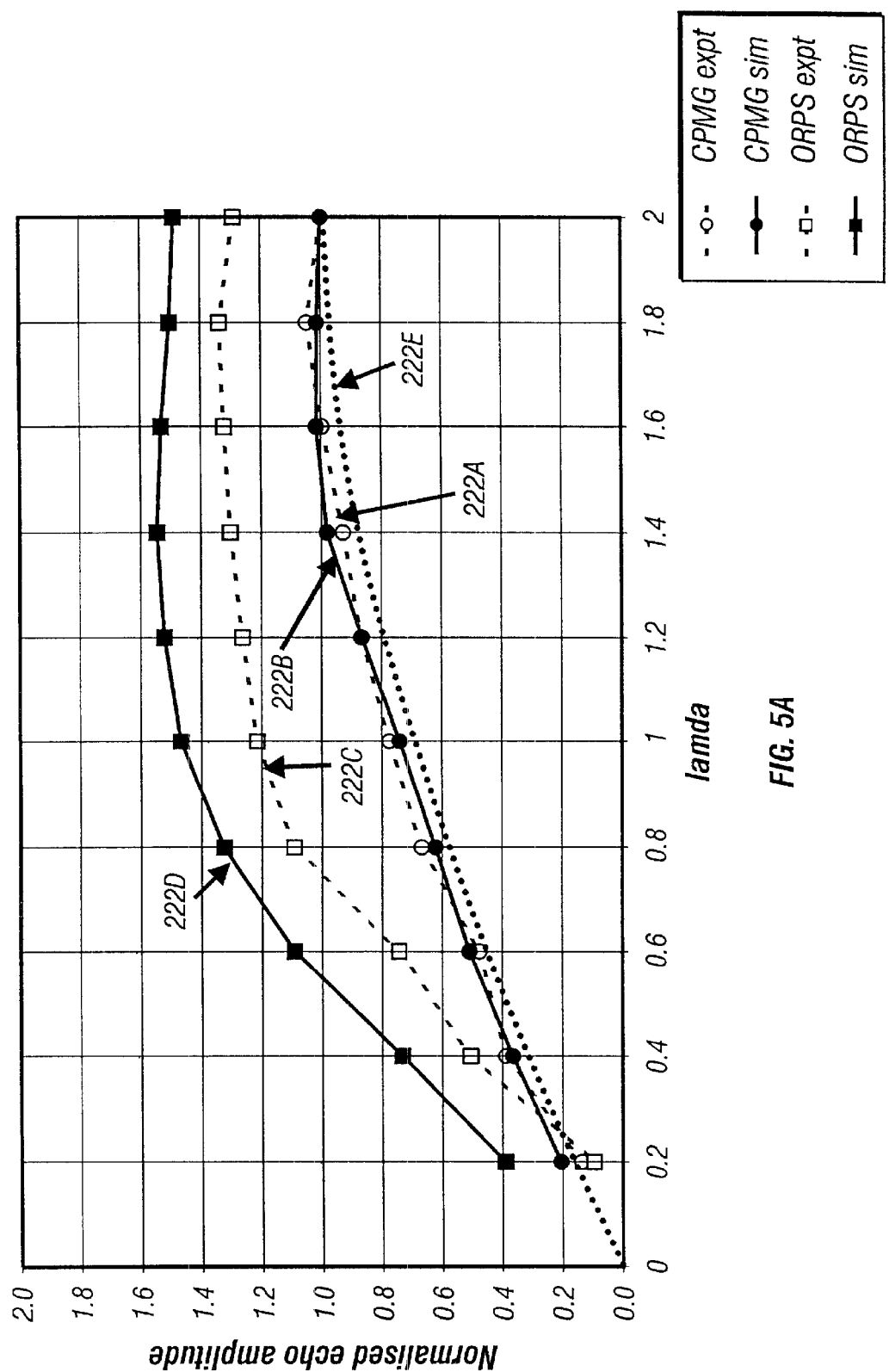
FIG. 5A is a graph of the echo amplitude as a function of the ratio of refocusing pulse to tipping pulse angle for the optimized pulse sequence in comparison with CPMG, for both experimental and simulated data.

Turning now to FIG. 5A, which is a plot compiled from data taken from the $3^{rd}$ echo of several sequences such as those shown in FIGS. 4A–D, plotted on the ordinate axis for different λ ratios (on the abscissa). It demonstrates the effect on echo amplitude of changing the refocusing pulse angle for sequences with different pulse timing. Curves 222A and 222B were obtained from experimental measurements and simulation results using the spin dynamics model respectively, for the exemplary logging tool using standard CPMG sequence pulse timing but varying the refocusing pulse length, and hence λ. Curves 222C and 222D were obtained from experiment and simulation respectively, for the same tool, using the optimized sequence timing of eq. (4) and varying the refocusing pulse length, and hence λ. The curves 222A and 222B were obtained with the duration $t_S$ equal to $t_{CP}$, as defined by the standard CPMG sequence. In contrast, the curves 222C and 222D were obtained with the duration $t_S$ equal to $t_{CP}$ minus half the tipping pulse duration (i.e.: $t_S = t_{CP} - T/2$). Curve 222E shows the result that would be expected when the refocusing pulse angle of a pulse sequence with standard CPMG timing ($t_S = t_{CP}$) is run in a homogeneous magnetic field, for comparison.

Still referring to FIG. 5A, in comparison to 222E, the curves 222A and 222B display an approximately flat response between λ=1.4 and λ=2, with a shallow peak at λ=1.7 evident in the simulated data (curve 222B), which is free from the random noise and consequent measurement error inherent in the experimental data. This implies that a good signal level will be obtained using refocusing pulses in the range 126° and 180°, with maximum signal obtained from a 153° pulse (λ=1.7); however a 126° refocusing pulse is preferred in practice because the shorter pulse results in a significant power saving benefit. Curves 222C and 222D, using the modified timing herein described, display an approximately flat response from λ2 right down to λ=1. The simulated data (curve 222D), displays a clear peak in echo amplitude at λ=1.4, corresponding to a refocusing pulse spin tip angle of 126°. Curves 222C and 222D both display enhanced signal amplitude over standard CPMG timing (222A and 222B) even at λ=2, although the degree of improvement is lower in the experimental data. The shape of the simulated and experimental curves is very similar in all cases. The relationship between echo amplitude, refocusing pulse angle and pulse timing can be shown to depend strongly upon the magnetic field gradients of the tool, and is clearly quite different to that expected from a system with homogeneous magnetic fields (curve 222E). The exemplary tool used in these studies had a static magnetic field optimized for minimum radial field gradient. A logging tool with a significant radial field gradient, such as that due to Shtrikman, would exhibit curves of a different shape; specifically, the degree of signal enhancement seen for 1.5<λ<2 when using sequences with standard CPMG timing ($t_S = t_{CP}$) would be increased compared to the exemplary design used here. Therefore, depending upon the tool design and resultant magnetic and RF field gradients of the tool, and the exact pulse sequence timing, refocusing pulse angles as low as 100° (λ~1.1) and as large as 170° (λ~1.9) will give optimum results.

One implication of the results in FIG. 5A is that a gain in signal level can be obtained by reducing the duration of the refocusing pulse so that it results in a tipping angle that is less than 180°. This effect would not occur in a tool with homogeneous and orthogonal static magnetic and RF fields. Furthermore, the reduction in refocusing pulse duration results in a commensurate reduction in RF duty cycle and a significant power saving, which is of great value in a downhole logging or MWD tool.

A further conclusion of the results of FIG. 5A is that a further very significant increase in echo amplitude can be obtained by shortening the $t_S$ period in relation to $t_{CP}$. In classical CPMG the following relation holds:

$$t_s = t_{cp} \qquad (5)$$

Referring to FIGS. 3A–C for clarification of the precise definition of $t_{CP}$ and $t_S$, in all sequences described herein $t_{CP}$ is half the time from echo-peak to echo-peak and also half the time from the center of one refocusing pulse to the center of the next. In standard CPMG the time from the end of the tipping pulse to the center of the first refocusing pulse is also equal to the same time period, $t_{CP}$, whilst in the novel sequence described herein, and defined in eq. (4), the equivalent wait period $t_S$, from the end of the tipping pulse T to the center of the first refocusing pulse R, is not equal to $t_{CP}$.

Figure 5B:
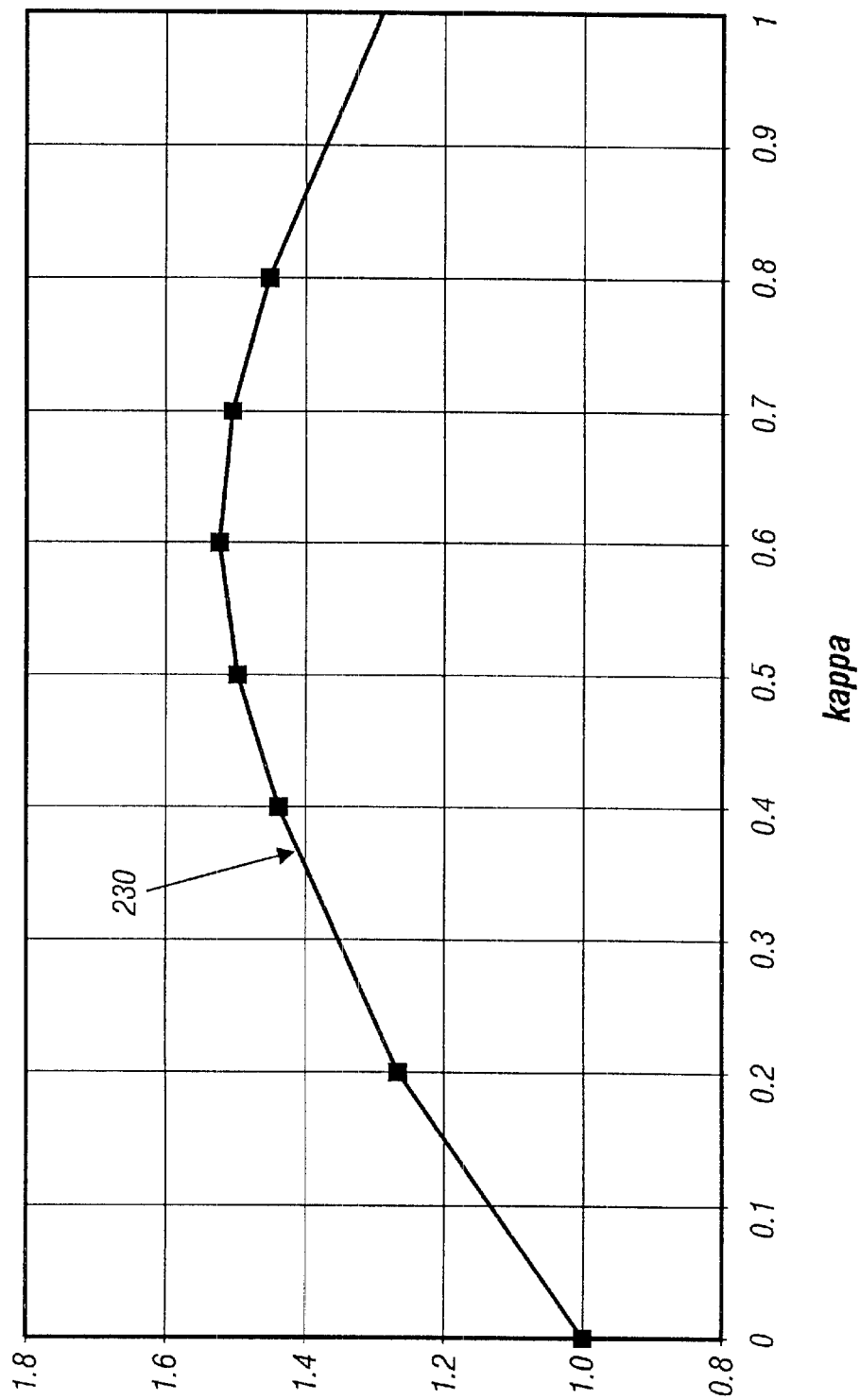
FIG. 5B is a graph of the variation of the echo amplitude as a function of the RF pulse timing parameter κ (simulated data only)

The maximum echo amplitude is obtained when the $t_S$ period is reduced by a fraction κ of the tipping pulse duration, T. As for the parameter λ, the optimum value for κ also depends on the magnetic and RF field shapes, but is typically near one half. The curve 230 in FIG. 5B shows the effect on the 3rd echo amplitude using the optimized pulse sequence of eq. (4) and varying κ, with λ held constant at 1.6. For the exemplary sensor used in the studies, with this λ value, the optimum κ is 0.6, providing a very valuable 50% increase in signal compared to the same sequence with standard CPMG timing (κ=0).

Therefore the relation between $t_S$ and $t_{CP}$ in the present invention is:

$$t_s = t_{cp} - \kappa T \qquad (6)$$

The sequence of eq. (4), with optimized λ and κ timing parameters, is designated herein as the Optimized Rephasing Pulse Sequence.

Another aspect of the Optimized Rephasing Pulse Sequence (ORPS) is the adjustment of the phases of the tipping pulses and the refocusing pulse in a series of pulse sequences. Kleinberg (U.S. Pat. No. 5,363,041) discusses the use of one such technique in which the phases of successive tipping pulses differ by π radians. In such a method, the second, fourth, sixth, etc. 90° tipping pulses have a phase that is shifted by π radians relative to the phase of the first, third, fifth, etc. tipping pulse. When the data are subsequently processed by subtracting CPMG echo trains in phase alternated pairs (PAPs) and adding the results to improve signal-to-noise, this technique cancels the baseline offset errors and ringing artefacts from the refocusing pulses. "Ringing" is the term applied to the unwanted signal originating from the recovery of the RF antenna from the high power RF pulse. This is minimized by tool design but can never be eliminated and is often significantly larger than the NMR echo signal. For correct operation of the tool it is necessary that this signal is removed by the phase cycling scheme described here. One phase cycling scheme used in the present invention is summarized in Table 1.

TABLE 1

| Sequence ID | Tipping pulse | All refocusing pulses |
|---|---|---|
| A | 0 | π/2 |
| B | π | π/2 |
| C | π/2 | 0 |
| D | −π/2 | 0 |

TABLE 2

| Sequence ID | Tipping pulse | All refocusing pulses |
|---|---|---|
| A | 0 | π/2 |
| B | 0 | −π/2 |
| C | π/2 | 0 |
| D | π/2 | π |

To demonstrate the efficacy of the method in removing the unwanted ringing signal from the refocusing pulse whilst preserving the NMR signal, the following symbols are defined: let $\alpha$ represents the NMR echo signal, $\beta$ represents the ringing signal from the initial tipping pulse, $\delta$ represents the ringing signal from the refocusing pulse, and $\sigma$ represents the stochastic noise. As previously described, all data must be acquired in phase quadrature and is therefore a vector quantity with an associated phase angle, which is here denoted by the value in brackets. The phase angles of the NMR echo signals and the ringing signals are all locked to the phases of the RF pulses within their associated pulse sequences, and hence to the phase of the demodulation carrier signal used in the spectrometer.

The data acquired during the four sequences of the phase cycling scheme described in Table 1 are therefore:

$$A = \alpha(0) + \beta(0) + \delta(\pi/2) + \sigma \quad (7a)$$

$$B = \alpha(\pi) + \beta(\pi) + \delta(\pi/2) + \sigma \quad (7b)$$

$$C = \alpha(\pi/2) + \beta(\pi/2) + \delta(0) + \sigma \quad (7c)$$

$$D = \alpha(-\pi/2) + \beta(-\pi/2) + \delta(0) + \sigma \quad (7d)$$

If the first pair of echo train data are subtracted and this is repeated for the second pair, and the resultant data is then added then, noting that the stochastic noise $\sigma$ has no phase coherence and therefore accumulates as the square root of the sum of the squares of the contributions from each data window, the result is:

$$(A-B) + (C-D) = 4\alpha(0) + 4\beta(0) + 2\sigma \quad (8)$$

Note that the second PAP data, (C−D), must be phase shifted by π/2 before adding to the first PAP, (A−B). This can easily be achieved mathematically after data acquisition, but is more usually achieved by the convenient method of shifting the phase of the demodulation signal during acquisition of the data. In order to clarify the method of the invention, all data will be assumed to have been acquired in the same phase, and PAP data subsequently phase shifted as required before adding. This four cycle scheme therefore removes the refocusing pulse ringing $\delta$, but the tipping pulse ringing $\beta$ remains and may contaminate early echoes in sequences with short inter-echo spacing. It will be clear that the second pair of phase alternated sequences, C and D, are not necessary for the cancellation of ringing and baseline errors, so a dual cycle, or single PAP, scheme is adequate:

$$(A-B) = 2\alpha(0) + 2\beta(0) + \sqrt{2}\sigma \quad (9)$$

Similarly, it is possible to leave the phases of subsequent tipping pulses the same from sequence to sequence and invert the phase of all refocusing pulses, as shown in Table 2:

Echo train data is then simply added to cancel baseline errors, according to:

$$(A+B+C+D) = 4\alpha(0) + 4\beta(0) + 2\sigma \quad (10)$$

producing the same result as eq. (8)

This method is slightly inferior to the scheme shown in Table 1 and eq. (8) as it relies on the ringing artefacts being exactly equal and opposite for the alternated phases of refocusing pulse phases; although this is generally true it is better to leave the refocusing pulses at the same phase in a PAP and invert the tipping pulse, which has lower RF energy and a generally smaller ringing signal.

One embodiment of the invention uses an additional inverse tipping pulse (i.e., a pulse with the same spin tip angle as the initial tipping pulse but phase shifted by π radians) at the end of the pulse sequence, according to:

$$W'-T_x-t_s-R_y-(t_{cp}-\text{echo}-t_{cp}-R_y)_j-t_{cp}-T_{-x} \quad (11)$$

Figures 5C, 5D:
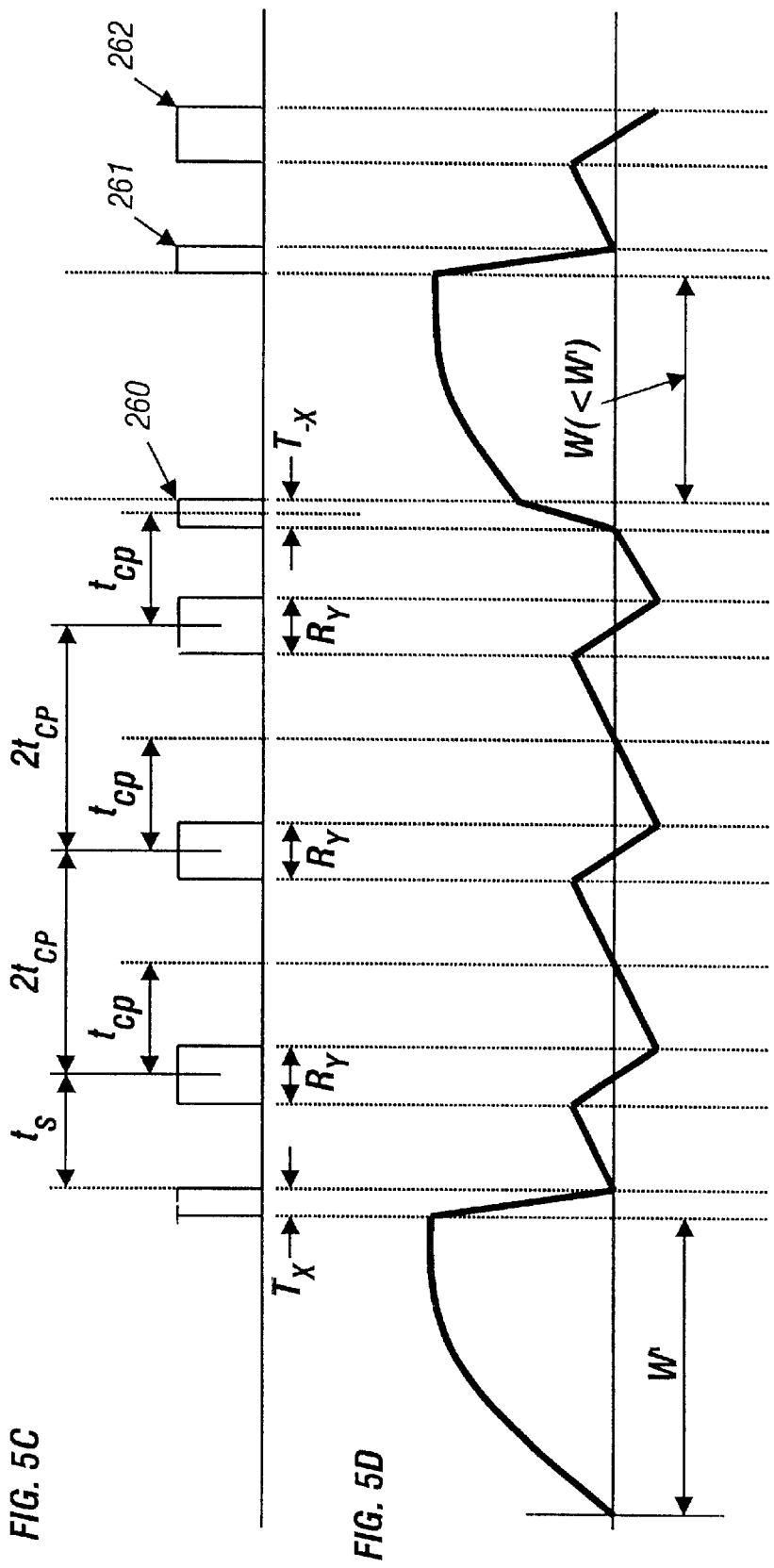
FIGS. 5C & 5D. show the application of the optional final forced recovery pulse.

The $T_{-x}$ pulse shown as 260, occurs at the same time as the formation of the final echo, as shown in FIG. 5C. The −X subscript indicates that the phase of the final pulse is inverted, or shifted by π radians, with respect to the phase of the initial tipping pulse $T_X$ and therefore acts about the −X axis. The effect of the final pulse is to rotate the nuclear spins that are in the process of forming the echo away from the transverse (XY) plane and back into substantial alignment with the magnetic field along the Z axis, as depicted in FIG. 5D. The spins would naturally return to alignment with the static field with time constant T1 but the additional $T_{-X}$ pulse causes a more rapid "forced recovery". For that reason, the $T_{-X}$ pulse at the end of the sequence may be referred to as the forced recovery or driven equilibrium pulse.

In one embodiment of the invention, the forced recovery pulse is used to reduce the recovery period W', thereby speeding up the acquisition of the NMR data so that more echo trains are collected in the same time period. In FIG. 5D the initial waiting period W at the start of the measurement should be greater than five T1 periods to ensure the longitudinal magnetization $M_Z$ is fully recovered. After a single sequence with a final forced recovery pulse, the waiting period for 100% recovery is reduced to W' which is less than W. Subsequent sequences also use the shorter wait period. At the end of this reduced wait time, another tipping pulse 261 is applied followed by a set of refocusing pulses, of which only one 262 is shown. The additional echo trains thereby collected can then be averaged to improve the signal to noise ratio. This method gives a particularly advantageous improvement in signal when applied to a sequence in which the wait period is intentionally shorter than five times the longest T1, so that only partial recovery of the long T1 components occurs (for example in a sequence designed to measure only the Bulk Volume Irreducible signal from a formation).

In another embodiment of the invention, the recovery period is not changed, and the natural recovery of the spin system is further progressed by the time the next pulse sequence is applied. This also results in an enhanced signal if the W period is less than five T1 periods. In both methods, not all of the spins are "captured" by the forced recovery pulse, so recovery is not complete and some recovery wait is always needed before pulsing again.

The concept of driven equilibrium has been used in NMR imaging to improve experiment repetition times and hence increase signal to noise ratio Becker at al. However, the forced recovery pulse has not been used to cancel the ringing artefact, as described below.

It will be apparent from examination of eqs. (8) and (10) that these commonly used phase cycling schemes such as those described in Tables 1 and 2, above, will not remove the ringing signal from the initial tipping pulse, because the ringing signal is always in phase with the tipping pulse. If ringing persists for longer than 2 $t_{cp}$ then it can corrupt the first and possibly subsequent echoes. It is desirable to reduce $t_{cp}$ to the minimum possible, typically 0.3 ms, for good data quality and this can result in the first one or two echoes being corrupted with ringing signal from the tipping pulse, requiring them to be discarded. The NMR signal component arising from clay-bound fluid in the formation rocks has a T2 typically of only a few milliseconds so these echoes are useful if the tool is to faithfully record the clay bound fluid signal. A modification to the pulse sequence is now described that allows the unwanted tipping pulse ringing signal to be removed, thus allowing the first few echoes to be retained and used for calculating the clay-bound fluid contribution. This sequence of pulses may be repeated with the echoes averaged to improve the signal to noise ratio.

Figure 5E:
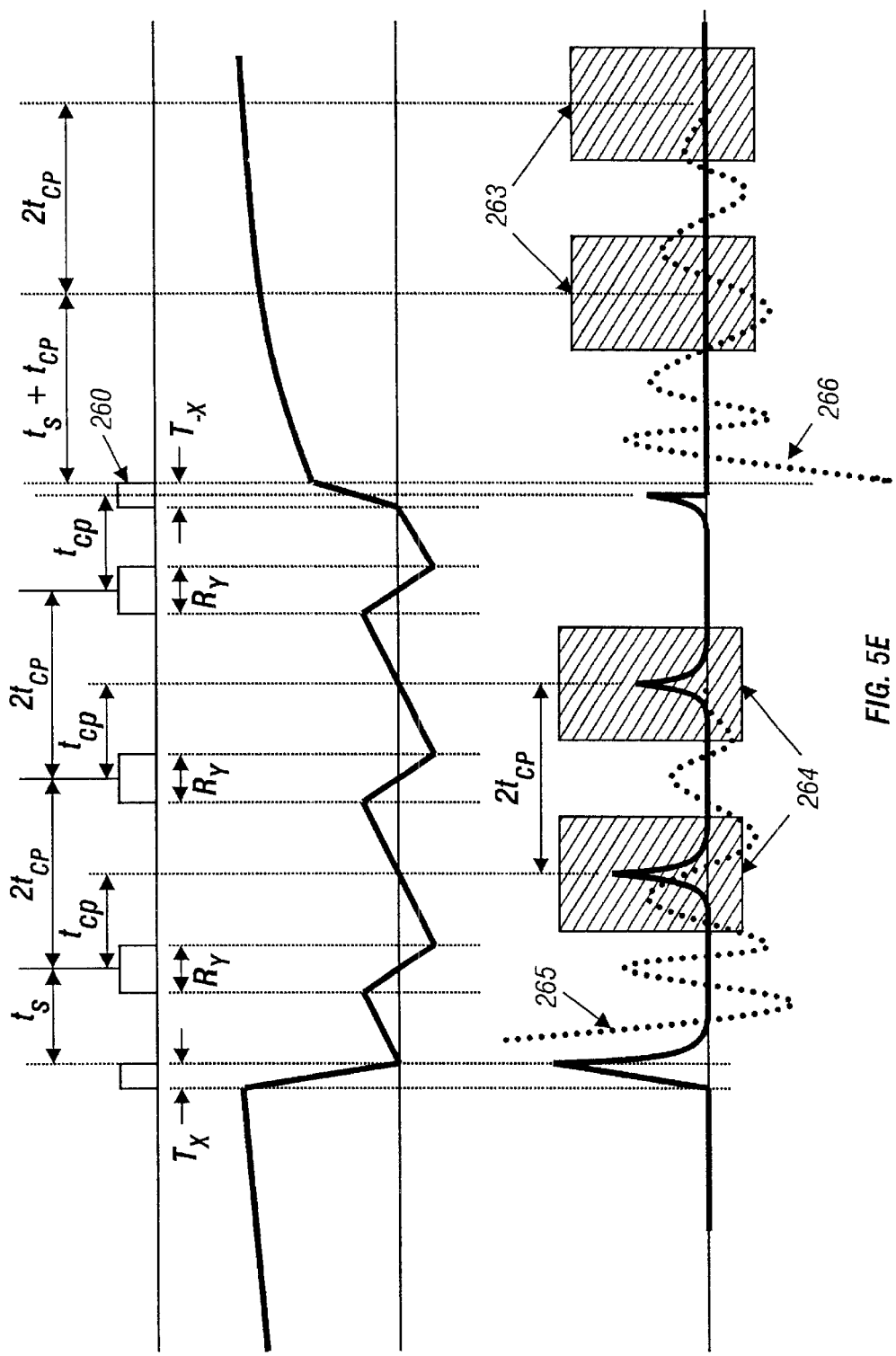
FIG. 5E shows the application of a forced recovery pulse in reducing the ringing artefact.

After the final $T_{-x}$ pulse of the sequence no more RF pulses are applied, so that the spin system loses coherence with time constant T2*. However, if the tool spectrometer continues to acquire data at 2 $t_{cp}$ intervals starting a suitably timed interval after the final pulse, as shown in FIG. 5E, depicting a sequence with only two echoes for clarity, then the data acquired, 266, will contain the ringing signal from the combined effect of the forced recovery pulse and the final refocusing pulse, plus stochastic noise, but no NMR signal, as the spin system has lost coherence. The data from windows 263 in FIG. 5E can subsequently be combined with the echo train data from windows 264 to remove the $T_x$ tipping pulse ringing signal, 265, from the first few echoes. This may then be followed by additional pairs of sequences, cycling through the available phases to remove all baseline artefacts, as required.

A typical phase cycling scheme to implement this method is shown in Table 3:

TABLE 3

| Sequence ID | Initial tipping pulse | All refocusing pulses | Forced recovery pulse |
|---|---|---|---|
| A | 0 | π/2 | π |
| B | π | π/2 | 0 |
| C | π/2 | 0 | −π/2 |
| D | −π/2 | 0 | π/2 |

Using the nomenclature previously established, but defining an additional parameter β' to represent the ringing signal from the final forced recovery pulse, the echo data equivalent to repeated windows 264 in FIG. 5E obtained from pulse sequences A to D in Table 3 is equal to eq. (7a) to (7d). Similarly the data acquired after the final forced recovery pulse, equivalent to repeated windows 263 in FIG. 5E can be denoted A' to D', and is equal to:

$$A'=\delta(\pi/2)+\beta'(\pi)+\sigma \quad (12a)$$

$$B'=\delta(\pi/2)+\beta'(0)+\sigma \quad (12b)$$

$$C'=\delta(0)+\beta'(-\pi/2)+\sigma \quad (12c)$$

$$D'=\delta(0)+\beta'(\pi/2)+\sigma \quad (12d)$$

It is important to note that in a well designed tool the ringing from an RF pulse is very repeatable, so the tipping pulse ringing b' is substantially equal in shape and amplitude to the forced recovery pulse ringing b', because it originates from a RF pulse of equal intensity and duration, but it is always inverted in phase, due to the inversion of the phase of the forced recovery pulse in relation to the phase of the tipping pulse in any one sequence. Therefore it follows that:

$$\beta(0)=-\beta'(\pi) \quad (13)$$

and $$\beta(-\pi/2)=-\beta'(\pi/2) \quad (14)$$

The NMR signal can be recovered, with no significant corruption by ringing from either tipping or refocusing pulses, by combining the data from the single PAP formed by sequences A and B on an echo by echo basis according to $$(A+A')-(B+B') \quad (15)$$

Using the relations (13) and (14) and, it can be calculated that eq. (15) reduces to $$(A+A')-(B+B')=2\alpha(0)+2\sigma \quad (16)$$

Only those echoes corrupted by ringing from the initial tipping pulse need processing in this fashion, the remainder are processed in the usual way, according to eq. (9); as there is no β ringing signal from the tipping pulse in these later echoes, eq. (9) reduces to:

$$A-B=2\alpha(0)+\sqrt{2}\sigma \quad (17)$$

Therefore the only penalty of the method is a $1/(\sqrt{2})$ factor reduction in signal to noise ratio for the echoes processed to remove tipping pulse ringing, due to the addition of stochastic noise without signal, as demonstrated by the ratio of the results of eqs. (17) and eqs. (16).

The resultant small loss in signal-to-noise-ratio in the echoes of a sequence processed to remove tipping pulse ringing can be taken into account during subsequent signal processing to derive the formation NMR properties.

The dual cycle phase cycling scheme of eqs. (16) and (17), which only uses the first two lines of Table 3, can be extended to a scheme with four cycles, or two PAPs, where the bulk of the echoes in a sequence are processed according to eq. (8) which reduces to $$(A-B)+(C-D)=4\alpha(0)+2\sigma \quad (18)$$

whilst those with tipping pulse ringing signal corruption are processed according to:

$$\{(A+A')-(B+B')\}+\{C+C')-(D+D')\}=4\alpha(0)+2\sqrt{2}\sigma \quad (19)$$

In both cases the phase of the second PAP must be shifted by π/2 before adding, as previously noted.

It is clear from a comparison of eqs. (8) and (19) that the improved method of signal processing herein described, in which data is acquired in windows after a final forced recovery pulse and used in the processing of the usual echo data, completely removes the unwanted tipping pulse ringing signal β.

Figure 6A:
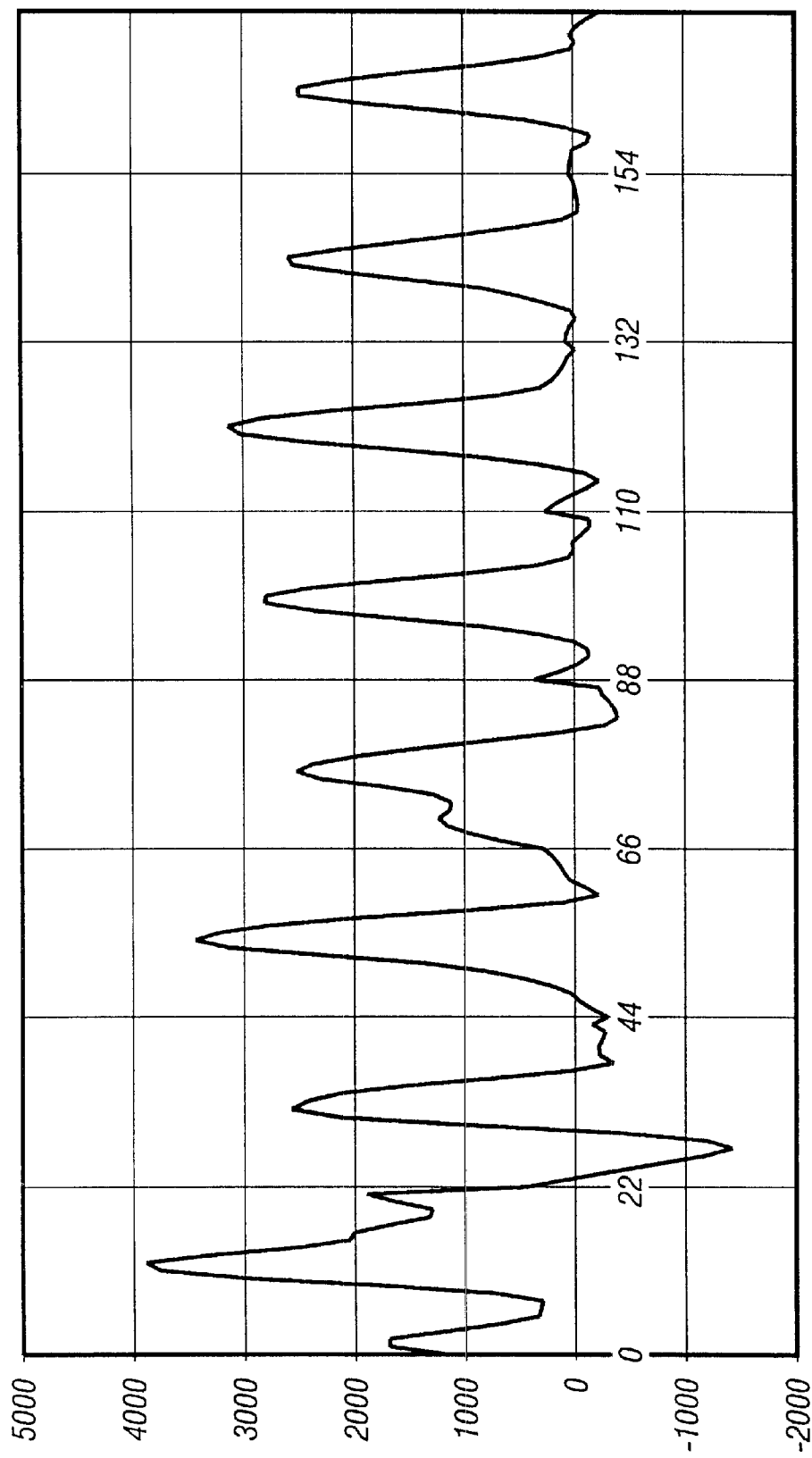
FIG. 6A is a data plot showing NMR echo signals from a tool with severe contamination by ringing signal from the tipping pulse.
Figure 6B:
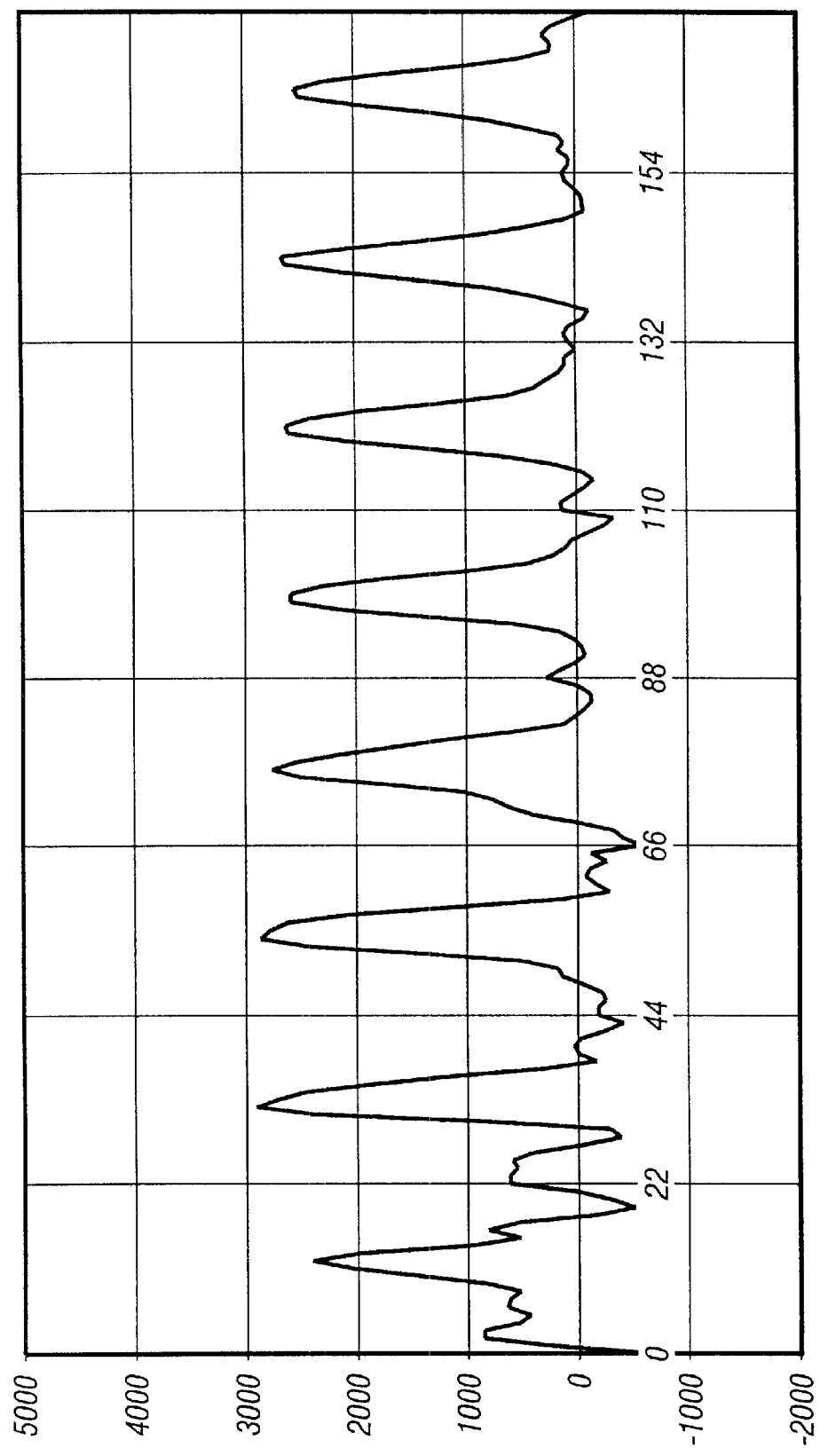
FIG. 6B is a data plot showing NMR echo signals from a tool in which severe contamination by ringing signal from the tipping pulse has been corrected by a processing method herein described.

FIG. 6A shows experimental data for an eight echo NMR measurement from an exemplary tool with a large ringing signal. The data set was processed according to the method of eq. (18) and, although ringing signal from the refocusing pulses has been successfully removed, there is still severe distortion of the echoes by residual ringing from the tipping pulse. This sequence was applied with a final forced recovery pulse, and ringing signal data acquired in the wait period at the intervals described. FIG. 6B shows the effect of re-processing the data according to the method of eq. (19). The distortion due to the ringing signal from the tipping pulse is significantly reduced.

In the same way that the phase cycling scheme of Table 1, used in conjunction with the data processing method of eq. (8), produces the same result as the phase cycling scheme of Table 2 used in conjunction with the data processing method of eq. (10), it will be clear that there are alternative methods to the phase cycling scheme of Table 3, used in conjunction with the data processing method of eq. (19) which will produce similar results. It is intended that the examples given illustrate all of those alternative methods pertaining to the processing of data acquired after a forced recovery pulse.

Another embodiment of the invention uses the forced recovery pulse in conjunction with a conventional CPMG sequence, i.e., one in which the refocusing pulse is 90° (i.e.: $\lambda=2$) and $t_s=t_{cp}$ (i.e.: $\kappa=1$).

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method for determining a parameter of interest of a volume of earth formation with a borehole tool conveyed in a borehole within the formation, the method comprising:

(a) using a magnet assembly on the borehole tool for producing a static magnetic field having a substantially uniform field strength in said volume of the formation and aligning nuclear spins within said volume parallel to a direction of the static field;

(b) producing a radio frequency (RF) magnetic field in said volume of the formation, said RF magnetic field having a direction substantially orthogonal to a direction of the static field, the RF field including a pulse sequence:

$$W-T-t_x-R-(t_{cp}-\text{echo}-t_{cp}-R)_j$$

wherein W is a wait period, T is a tipping pulse for tipping the nuclear spins at an angle substantially equal to ninety degrees to cause precession thereof, $t_s$ is a waiting time, $t_{CP}$ is the Carr-Purcell time, R is a refocusing pulse for having a spin tip angle less a 180° pulse, and j=1, 2, . . . J, and J is the number of echoes collected in a single sequence of pulses;

(c) measuring with a receiver coil on the borehole tool magnetic resonance signals induced by the pulsed RF field in the formation, said signals having a higher signal-to-noise ratio than a pulse sequence wherein said refocusing pulse is a 180° pulse; and (d) processing said measured signals to determine the parameter of interest.

2. The method of claim 1 wherein the carrier phase of substantially all of said refocusing pulses in said pulse sequence is shifted by $\pi/2$ with respect to a phase of the tipping pulse.

3. The method of claim 2 wherein a ratio of the tipping angle of a refocusing pulse to the tipping angle of the tipping pulse is factor having a value less than 2.0.

4. The method of claim 3 wherein said factor is between 1.1 and 1.9.

5. The method of claim 3 wherein said factor is determined by at least one of (i) experimental measurements using the tool, and, (ii) a numerical simulation of a response of the tool.

6. The method of claim 2 wherein said wait time $t_s$ is related to the Carr-Purcell time $t_{cp}$ and a duration T of the tipping pulse by a relation of the form $t_s=t_{cp}-\kappa T$.

7. The method of claim 6 wherein $\kappa$ is determined by at least one of (i) experimental measurements with the tool, and, (ii) a numerical simulation of a response of the tool.

8. The method of claim 7 wherein $\kappa$ has a value between 0.2 and 1.0.

9. The method of claim 2 further comprising repeating steps (b) and (c) of claim 1 at least once wherein the tipping pulse T of the first pulse sequence is phase shifted by 0 radians, and the tipping pulse of the second sequence is phase shifted by $\pi$ radians with respect to the phase of a continuous wave Larmor frequency signal, and wherein results measured in repeated step (c) are subtracted from results measured in step (c) to provide a first corrected measurement.

10. The method of claim 9 further comprising repeating steps (b) and (c) of claim 1, wherein in a third pulse sequence, said tipping pulse is phase shifted by $\pi/2$, and in a fourth pulse sequence, said tipping pulse is phase shifted by $-\pi/2$ with respect to said continuous wave Larmor frequency signal and wherein results measured in step (c) of the fourth pulse sequence are subtracted from results measured in step (c) of the third pulse sequence and the result added to the first corrected measurement to provide a second corrected measurement.

11. The method of claim 2 wherein said pulse sequence includes at its end an additional forced recovery pulse T', at a time corresponding to a time of an echo, said additional pulse having a phase shifted by $\pi$ radians with respect to the phase of the tipping pulse, said additional pulse tending to re-align said nuclear spins parallel to the direction of the static field.

12. The method of claim 11 further comprising repeating steps (b) and (c) of claim 1 at least once, and wherein the wait time for the second and any subsequent pulse sequences is less than the wait time for the first pulse sequence.

13. The method of claim 11 wherein said measured signals in the receiver include a ringing artefact, the method further comprising measuring an additional signal induced in said receiver coil by said forced recovery pulse and using said additional signal to reduce said ringing artefact.

14. The method of claim 13 wherein measuring said additional signal further comprises making measurements within time windows, the first such window centered at $t_s+t_{cp}$ after the forced recovery pulse and subsequent windows spaced at 2 $t_{CP}$ intervals.

15. The method of claim 14 further comprising repeating steps (b) and (c) of claim 1 wherein in a first pulse sequence said tipping pulse is phase shifted by 0 radians, and in a second pulse said tipping pulse is phase shifted by $\pi$ radians, with respect to a continuous wave Larmor frequency signal, and wherein results measured in step (c) and repeated step (c) are subtracted from each other to provide a first corrected measurement.

16. The method of claim 15 further comprising repeating steps (b) and (c) wherein in a third pulse sequence, said tipping pulse is phase shifted by $\pi/2$, and in a fourth pulse sequence, said tipping pulse is phase shifted by $-\pi/2$, with respect to said continuous wave Larmor frequency signal, and wherein results measured in step (c) and repeated step (c) are subtracted from each other and the result added to the first corrected measurement to provide a second corrected measurement.

17. A method for determining a parameter of interest of a volume of earth formation with a borehole tool conveyed in a borehole within the formation, themethod comprising:

(a) using a magnet assembly on the borehole tool for producing a static magnetic field having a substantially uniform field strength in said volume of the formation and aligning nuclear spins within said volume parallel to a direction of the static field;

(b) producing a radio frequency (RF) magnetic field in said volume of the formation, said RF magnetic field having a direction substantially orthogonal to a direction of the static field, the RF field including a pulse sequence:

$$W-T-(t_{cp}-\text{echo}-t_{cp}-R)_j-t_{cp}-T'$$

wherein W is a wait period, T is a tipping pulse for tipping the nuclear spins at an angle substantially equal to ninety degrees to cause precession thereof, $t_{cp}$ is the Carr-Purcell time, R is a 180° refocusing pulse, j=1, 2, ... J, and J is the number of echoes collected in a single sequence of pulses, and T' is a forced recovery pulse for aligning the nuclear spins substantially parallel to the direction of the static field;

(c) measuring with a receiver coil on the borehole tool magnetic resonance signals induced by the pulsed RF field in the formation said measured signals including a ringing artefact; and (d) processing said measured signals to determine the parameter of interest wherein processing said measured signals further comprises using a portion of the measured signals attributable to the ringing artefact of the forced recovery pulse to reduce said ringing artefact in the rest of the measured signals.

18. The method of claim 17 wherein the carrier phase of substantially all of said refocusing pulses is shifted by π/2 radians with respect to a phase of the tipping pulse.

19. The method of claim 17 wherein said portion of the measured signal attributable to the ringing artefact of the forced recovery signal further comprises a first time window centered $t_s+t_{cp}$ after the forced recovery pulse.

20. The method of claim 19 wherein said portion of the measured signal attributable to the ringing artefact of the forced recovery signal further comprises at least one additional time window at a time $2 t_{cp}$ after the first time window.

21. The method of claim 18 further comprising repeating steps (b) and (c) of claim 17 wherein in a first pulse sequence said tipping pulse is phase shifted by 0 radians, and in a second pulse sequence said tipping pulse is phase shifted by π radians, with respect to a continuous wave Larmor frequency signal, and wherein results measured repeated step (c) are subtracted from results measured in step (c) to provide a first corrected measurement.

22. The method of claim 21 further comprising repeating steps (b) and (c) of claim 17 for said volume of said formation, wherein in a third pulse sequence, said tipping pulse is phase shifted by π/2 radians, and in a fourth pulse sequence, said tipping pulse is phase shifted by –π/2 radians, with respect to said continuous wave Larmor frequency signal, and wherein results measured in step (c) of the fourth sequence are subtracted from results measured in step (c) of the third sequence and the result added to the first corrected measurement to give a second corrected measurement.

23. A method for determining a parameter of interest of a volume of earth formation with a borehole tool conveyed in a borehole within the formation, the method comprising:

(a) using a magnet assembly on the borehole tool for producing a static magnetic field having a substantially uniform field strength in said volume of the formation and aligning nuclear spins within said volume parallel to a direction of the static field;

(b) producing a radio frequency (RF) magnetic field in said volume of the formation, said RF magnetic field having a direction substantially orthogonal to a direction of the static field, the RF field including a pulse sequence:

$$W-T-t_s-R-(t_{cp}-\text{echo}-t_{cp}-R)_j$$

wherein W is a wait time, T is a tipping pulse for tipping the nuclear spins at an angle substantially equal to ninety degrees to cause precession thereof, $t_S$ is a waiting time, $t_{cp}$ is the Carr-Purcell time, R is a refocusing pulse, j=1, 2, ... J, and J is the number of echoes collected in a single sequence of pulses, wherein $t_S$ is less than $t_{cp}$;

(c) measuring with a receiver coil on the tool magnetic resonance signals induced by the pulsed RF field in the formation; and (d) processing said measure signals to determine the parameter of interest.

24. The method of claim 23 wherein the carrier phase of substantially all of said refocusing pulses is shifted by π/2 radians with respect to the tipping pulse.

25. The method of claim 24 wherein a ratio of the tipping angle of the refocusing pulse to the tipping angle of the tipping pulse is a first factor having a value less than 2.0.

26. The method of claim 25 wherein said first factor is between 1.1 and 1.9.

27. The method of claim 25 wherein said first factor is determined by at least one of (i) experimental measurements using the tool, and, (ii) a numerical simulation of a response of the tool.

28. The method of claim 27 wherein said wait time $t_S$ is related to the Carr-Purcell time $t_{CP}$ and a duration T of the tipping pulse by a relation of the form $t_s=t_{cp}-\kappa T$.

29. The method of claim 28 wherein κ is determined by at least one of (i) experimental measurements with the tool, and, (ii) a numerical simulation of the tool.

30. The method of claim 29 wherein κ has a value less than 1.0

31. The method of claim 29 wherein κ has a value between 0.2 and 1.0

32. The method of claim 24 further comprising repeating steps (b) and (c) of claim 23 wherein in a first pulse sequence said tipping pulse is phase shifted by 0 radians, and in a second pulse sequence said tipping pulse is phase shifted by π radians, with respect to a continuous wave Larmor frequency signal, and wherein results measured in repeated step (c) are subtracted from results measured in step (c) to provide a first corrected measurement.

33. The method of claim 32 further comprising repeating steps (b) and (c) for said volume of said formation, wherein in a third pulse sequence, said tipping pulse is phase shifted by π/2 radians, and in a fourth pulse sequence, said tipping pulse is phase shifted by –π/2 radians, with respect to said continuous wave Larmor frequency signal, and wherein results measured in step (c) of the fourth pulse sequence are subtracted from results measured in and step (c) of the third pulse sequence and the result added to the first corrected measurement to provide a second corrected measurement.

34. The method of claim 1 wherein the carrier phase of substantially all of said refocusing pulses is shifted by between π/4 and 3π/4 radians with respect to the tipping pulse.

35. The method of claim 17 wherein the carrier phase of substantially all of said refocusing pulses is shifted by between π/4 and 3π/4 radians with respect to the tipping pulse.

36. The method of claim 23 wherein the carrier phase of substantially all of said refocusing pulses is shifted by between π/4 and 3π/4 radians with respect to the tipping pulse.

37. The method of claim 18 further comprising repeating steps (b) and (c) of claim 17 at least once, and wherein the wait time for the second and any subsequent pulse sequences is less than the wait time for the first pulse sequence.

* * * * *

UNITED STATES PATENT AND TRADEMARK OFFICE
CERTIFICATE OF CORRECTION

PATENT NO.    : 6,466,013 B1
DATED         : October 15, 2002
INVENTOR(S)   : Robert Hawkes, Robert Slade and Alun Lucas It is certified that error appears in the above-identified patent and that said Letters Patent is hereby corrected as shown below:

<u>Title page,</u>
Item [73], Assignee, "Baker Hughes Incorporated, Houston, TX (US)", should read -- Baker Hughes Incorporated, Houston, TX (US) and Oxford Instruments Superconductivity Ltd., Eynsham, Oxford, UK --.

Signed and Sealed this

Twenty-first Day of January, 2003

JAMES E. ROGAN
*Director of the United States Patent and Trademark Office*